(12) United States Patent
Inoue

(10) Patent No.: US 9,851,282 B2
(45) Date of Patent: Dec. 26, 2017

(54) SAMPLE COOLING DEVICE, AND AUTOSAMPLER PROVIDED WITH THE SAME

(71) Applicant: SHIMADZU CORPORATION, Kyoto-shi, Kyoto (JP)

(72) Inventor: Takashi Inoue, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 14/759,118

(22) PCT Filed: Mar. 29, 2013

(86) PCT No.: PCT/JP2013/059545
§ 371 (c)(1),
(2) Date: Jul. 2, 2015

(87) PCT Pub. No.: WO2014/155674
PCT Pub. Date: Oct. 2, 2014

(65) Prior Publication Data
US 2015/0346069 A1   Dec. 3, 2015

(51) Int. Cl.
*G01N 1/42*   (2006.01)
*G01N 30/24*   (2006.01)
(Continued)

(52) U.S. Cl.
CPC ............. *G01N 1/42* (2013.01); *G01N 30/16* (2013.01); *G01N 30/24* (2013.01); *G01N 30/06* (2013.01);
(Continued)

(58) Field of Classification Search
None
See application file for complete search history.

(56) References Cited

U.S. PATENT DOCUMENTS

| | | | |
|---|---|---|---|
| 4,964,734 A * | 10/1990 | Yoshida | G01N 5/045 177/245 |
| 6,170,267 B1 * | 1/2001 | Kitaoka | B01L 7/00 62/3.6 |

(Continued)

FOREIGN PATENT DOCUMENTS

| | | |
|---|---|---|
| CN | 102656738 A | 9/2012 |
| JP | 59167642 A | 9/1984 |

(Continued)

OTHER PUBLICATIONS

Communication dated May 4, 2016 issued by the State Intellectual Property Office of the People's Republic of China in counterpart application No. 201380075183.7.

(Continued)

*Primary Examiner* — Paul West
*Assistant Examiner* — Mark A Shabman
(74) *Attorney, Agent, or Firm* — Sughrue Mion, PLLC

(57) ABSTRACT

There are provided a sample cooling device capable of preventing air containing moisture from flowing into an accommodating chamber from outside the accommodating chamber, and of desirably dehumidifying air inside the accommodating chamber, and an autosampler provided with the same. Air is sent into an accommodating chamber 11 by a blower section 100 from outside the accommodating chamber 11 and the air is cooled by a dehumidifier section 13 to thereby cause dehumidified air to be supplied into the accommodating chamber 11. With the air sent into the accommodating chamber 11 by the blower section 100 from outside the accommodating chamber 11, the inside of the accommodating chamber 11 may be placed in a pressurized state. Since dehumidified air is supplied into the accommodating chamber 11 by air sent into the accommodating chamber 11 by the blower section 100 from outside the accommodating chamber 11 being cooled by the dehumidi- (Continued)

fier section 13, the humidity inside the accommodating chamber 11 may be prevented from rising due to the air that is sent from the blower section 100.

4 Claims, 1 Drawing Sheet

(51) Int. Cl.
*G01N 30/16* (2006.01)
*G01N 30/06* (2006.01)
*G01N 30/18* (2006.01)
*G01N 35/00* (2006.01)

(52) U.S. Cl.
CPC ... *G01N 30/18* (2013.01); *G01N 2035/00445* (2013.01)

(56) References Cited

U.S. PATENT DOCUMENTS

| | | |
|---|---|---|
| 2010/0248346 A1 | 9/2010 | Kaneko et al. |
| 2012/0312161 A1 | 12/2012 | Reitzle et al. |

FOREIGN PATENT DOCUMENTS

| | | |
|---|---|---|
| JP | 4135648 A | 5/1992 |
| JP | 06-129672 A | 5/1994 |
| JP | 85245 A | 1/1996 |
| JP | 2000-074801 A | 3/2000 |
| JP | 2000-074802 A | 3/2000 |
| JP | 2001-117016 A | 4/2001 |
| JP | 2002-022214 A | 1/2002 |
| JP | 2005233867 A | 9/2005 |
| JP | 2009-270857 A | 11/2009 |
| JP | 2010-237021 A | 10/2010 |

OTHER PUBLICATIONS

International Written Opinion of PCT/JP2013/059545, dated Apr. 23, 2013 [PCT/ISA/237].
International Search Report of PCT/JP2013/059545 dated Apr. 23, 2013 [PCT/ISA/210].
Communication dated Apr. 26, 2016, from the Japanese Patent Office in counterpart application No. 2015-507873.
Communication dated Jan. 10, 2017 from the Japanese Patent Office in corresponding Japanese Application No. 2015-507873.
Communication dated Dec. 15, 2016, from the State Intellectual Property Office of People's Republic of China in corresponding Application No. 201380075183.7.

\* cited by examiner

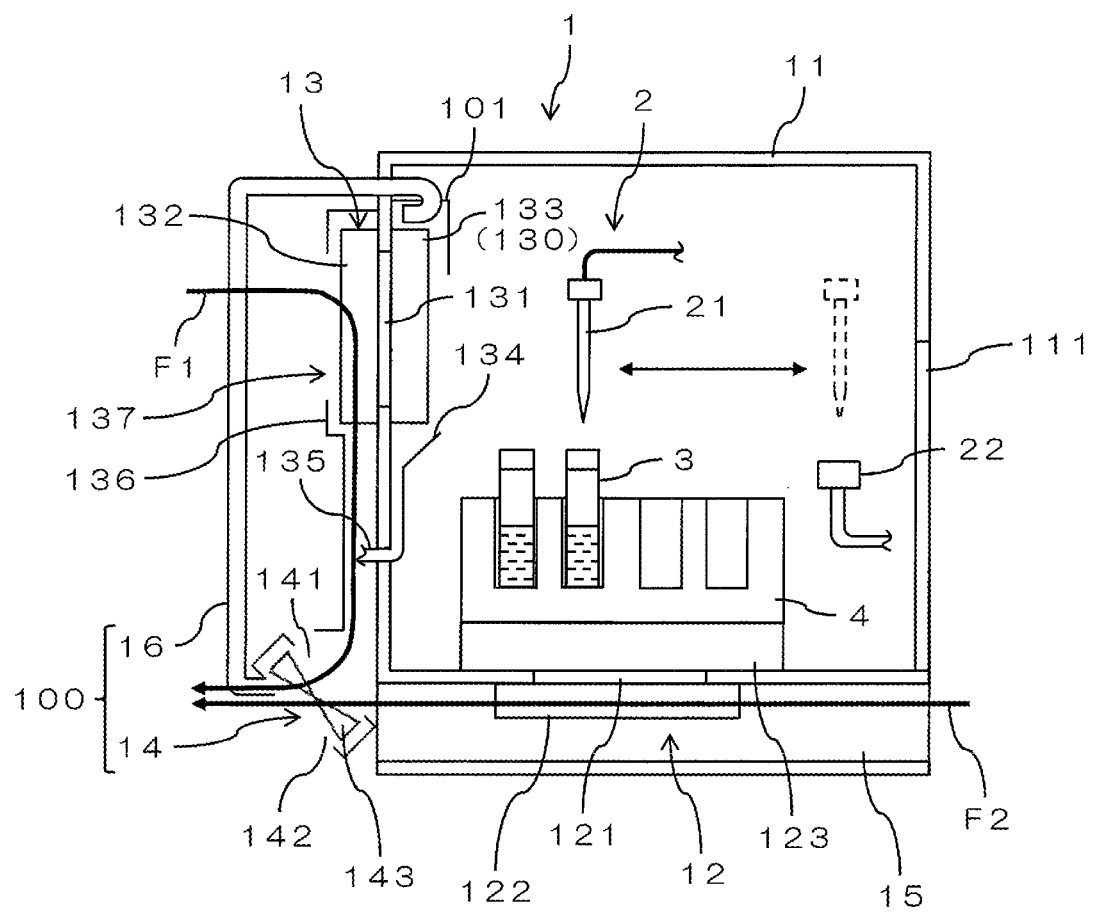

SAMPLE COOLING DEVICE, AND AUTOSAMPLER PROVIDED WITH THE SAME

CROSS REFERENCE TO RELATED APPLICATIONS

This application is a National Stage of International Application No. PCT/JP2013/059545, filed Mar. 29, 2013, the contents of which are incorporated herein by reference in its entirety.

TECHNICAL FIELD

The present invention relates to a sample cooling device for cooling a sample in a sample container that is accommodated in an accommodating chamber, and an autosampler provided with the same.

BACKGROUND ART

For example, some analysis devices such as a liquid chromatograph are provided with an autosampler for sucking a sample in a sample container by a needle and for automatically analyzing the sample. Depending on the type of sample to be the analysis target, the sample may sometimes have to be cooled from the standpoint of preventing alteration. In such a case, the sample in the sample container may be cooled by using a sample cooling device (for example, see Patent Document 1).

Regarding the sample cooling device, a direct cooling type and an air cooling type are known, for example. According to a direct-cooling sample cooling device, for example, a plurality of sample containers are accommodated in a highly thermal conductive rack and the rack is installed in a cooling section so that the sample containers on the rack may be cooled by a cooler such as a Peltier device provided to the cooling section. That is, with the direct-cooling sample cooling device, the cooling section configures an installation section for installing the sample containers. On the other hand, according to an air-cooling sample cooling device, a sample container may be cooled by air, by cooling the air inside an accommodating chamber accommodating the sample container by a cooler.

PRIOR ART DOCUMENTS

Patent Documents

JP 2000-74802 A

SUMMARY OF THE INVENTION

Problems to be Solved by the Invention

With a sample cooling device as described above, moisture in the air inside an accommodating chamber where a sample container is accommodated may be condensed at the time of cooling of a sample, and the moisture may negatively affect analysis of the sample. For example, if moisture is condensed on a sample container at an autosampler, the moisture on the sample container possibly gets mixed in the sample at the time of insertion of a needle into the sample container, thereby changing the concentration of the sample.

To suppress such a problem caused by condensation, a sample cooling device disclosed in Patent Document 1 adopts a structure where dehumidification is performed by cooling the air inside the accommodating chamber. Specifically, by causing the set temperature of a dehumidifier section to be near the dew point, the moisture in the air inside the accommodating chamber is condensed at the dehumidifier section, and the absolute humidity inside the accommodating chamber may be reduced.

Normally, a packing for maintaining air-tightness is attached to the boundary section of parts forming the accommodating chamber, and air containing moisture may be prevented from flowing into the accommodating chamber from outside the accommodating chamber. However, even with such a configuration, air may sometimes flow into the accommodating chamber from a gap between the parts forming the accommodating chamber. If air containing moisture flows into the accommodating chamber, the air inside the accommodating chamber may not be desirably dehumidified, and problems may be caused due to condensation as described above.

Particularly, with a sample cooling device, the temperature inside the accommodating chamber is relatively low, and the pressure inside the accommodating chamber is inclined to become negative. Thus, there is a problem that air may easily flow into the accommodating chamber from the gap between the parts forming the accommodating chamber. Also, air is sometimes made to flow on the outside the accommodating chamber so as to cool a heat generating section (for example, a switching power supply) in the periphery of the sample cooling device, and also in such a case, air may easily flow into the accommodating chamber from the gap between parts forming the accommodating chamber.

Moreover, with an autosampler provided with the sample cooling device as described above, a liquid drain port for draining cleaning liquid at the time of cleaning a flow path that is communicated with a needle is sometimes formed to a wall surface of the accommodating chamber. In this case, when liquid is not being drained from the liquid drain port, air containing moisture may flow into the accommodating chamber from outside the accommodating chamber through the liquid drain port.

The present invention has been made in view of the above circumstances, and has its object to provide a sample cooling device capable of preventing air containing moisture from flowing into an accommodating chamber from outside the accommodating chamber and of desirably dehumidifying the air inside the accommodating chamber, and an autosampler provided with the same.

Means for Solving the Problems

A sample cooling device of the present invention is a sample cooling device for cooling a sample in a sample container that is accommodated in an accommodating chamber, the sample cooling device including: a cooling section configured to cool the sample container that is accommodated in the accommodating chamber; a dehumidifier section configured to perform dehumidification by cooling air inside the accommodating chamber; and a blower section configured to supply dehumidified air into the accommodating chamber by sending air into the accommodating chamber from outside the accommodating chamber and causing the air to be cooled by the dehumidifier section.

According to such a configuration, with the air sent into the accommodating chamber by the blower section from outside the accommodating chamber, the inside of the accommodating chamber may be placed in a pressurized state. The air inside the accommodating chamber may thereby be caused to flow out of the accommodating chamber through, for example, the gap between the parts forming the accommodating chamber, and air containing moisture may be prevented from flowing into the accommodating chamber through the gap or the like.

Also, since air that is sent into the accommodating chamber by the blower section from outside the accommodating chamber is cooled by the dehumidifier section, dehumidified air is supplied into the accommodating chamber, and thus humidity inside the accommodating chamber may be prevented from rising due to the air that is sent in by the blower section. Accordingly, air containing moisture may be prevented from flowing into the accommodating chamber from outside the accommodating chamber, and the air inside the accommodating chamber may be desirably dehumidified.

The blower section may send a part of air that is sent from a cooling fan for cooling a heat generating section into the accommodating chamber.

According to such a configuration, air may be sent into the accommodating chamber from outside the accommodating chamber by using air that is sent by the cooling fan for cooling a heat generating section. Therefore, since there is no need to separately provide a fan or the like to send air into the accommodating chamber from outside the accommodating chamber, the manufacturing cost may be reduced.

The cooling fan may be one for cooling a heat generating section at the dehumidifier section. In this case, since the cooling fan and the dehumidifier section are placed relatively close to each other, a part of the air sent by the cooling fan may be cooled at the dehumidifier section by a simple configuration, and dehumidified air may be supplied into the accommodating chamber. The configuration may thus be simplified, and the manufacturing cost may be further reduced.

The dehumidifier section may include a cooling surface for cooling air inside the accommodating chamber. In this case, the blower section may send air from outside the accommodating chamber to near the cooling surface.

According to such a configuration, air sent into the accommodating chamber by the blower section from outside the accommodating chamber is sent to near the cooling surface of the dehumidifier section for cooling the air inside the accommodating chamber, and is thus desirably cooled at the cooling surface. Therefore, sufficiently dehumidified air may be supplied into the accommodating chamber, and thus humidity inside the accommodating chamber may be effectively prevented from rising due to the air that is sent in by the blower section.

An autosampler of the present invention includes: the sample cooling device; and a suction mechanism configured to suck a sample inside the sample container that is accommodated in the accommodating chamber.

Effects of the Invention

According to the present invention, with the air sent into the accommodating chamber by the blower section from outside the accommodating chamber, the inside of the accommodating chamber may be placed in a pressurized state, and also by cooling, by the dehumidifier section, the air that is sent into the accommodating chamber by the blower section from outside the accommodating chamber, dehumidified air is supplied into the accommodating chamber, and thus air containing moisture may be prevented from flowing into the accommodating chamber from outside the accommodating chamber, and the air inside the accommodating chamber may be desirably dehumidified.

BRIEF DESCRIPTION OF THE DRAWINGS

FIG. 1 is a diagram showing an example configuration of an autosampler according to an embodiment of the present invention.

MODE FOR CARRYING OUT THE INVENTION

FIG. 1 is a diagram showing an example configuration of an autosampler according to an embodiment of the present invention. This autosampler may be applied to various analysis devices such as a liquid chromatograph, for example.

The autosampler according to the present embodiment includes a sample cooling device 1 for cooling a sample, and a suction mechanism 2 for sucking the sample that is being cooled by the sample cooling device 1. The sample is contained in a sample container 3 such as a vial, and a plurality of the sample containers 3 may be installed inside the sample cooling device 1 by being held by a rack 4. The rack 4 is formed of a highly thermal conductive metal, for example.

The sample cooling device 1 includes an accommodating chamber 11, a cooling section 12, a dehumidifier section 13, and the like, for example. The accommodating chamber 11 has its wall surface formed of a highly heat insulating material, for example, and the accommodating chamber 11 may be hermetically sealed while accommodating inside the sample container 3 together with the rack 4. By cooling the sample container 3 that is accommodated in the accommodating chamber 11, the sample in the sample container 3 may be cooled.

The cooling section 12 is for cooling the sample container 3 that is accommodated in the accommodating chamber 11, and includes a Peltier device 121, a heat sink fin 122, an installation section 123, and the like, for example. The Peltier device 121 is provided in such a way as to partition the inside and the outside of the accommodating chamber 11, and for example, the heat sink fin 122 is attached on the Peltier device 121, on the surface on the outside of the chamber (the lower side), and the installation section 123 is attached on the Peltier device 121, on the surface on the inside of the chamber (the upper side).

The installation section 123 is formed of a highly thermal conductive metal, for example, and the rack 4 may be installed above the installation section 123. The installation section 123 may thereby be cooled by the Peltier device 121, and the sample container 3 on the rack 4 may be cooled through the installation section 123. At this time, the heat that is absorbed by the Peltier device 121 from the installation section 123 is radiated outside the accommodating chamber 11 via the heat sink fin 122.

In this manner, in the present embodiment, the cooling section 12 configures the installation section 123 where the sample container 3 is to be installed. That is, the sample cooling device 1 according to the present embodiment is a direct cooling type, and by installing the rack 4 at the cooling section 12, the sample container 3 on the rack 4 may be cooled.

A part of a wall surface of the accommodating chamber 11 forms an opening/closing cover 111 that is to be opened or closed, for example, at the time of installation of the sample container 3 inside the accommodating chamber 11. The opening/closing cover 111 is of a pullout type, for example, and the rack 4 may easily be installed on the installation section 123 of the cooling section 12 by the installation section 123 being moved forward according to an operation of pulling out the opening/closing cover 111 forward. A packing (not shown) for maintaining air-tightness is attached to the peripheral portion of the opening/closing cover 111, for example.

The dehumidifier section 13 is for performing dehumidification by cooling the air inside the accommodating chamber 11, and includes a Peltier device 131, a heat sink fin 132, an attachment section 133, a tray 134, a drainpipe 135, and the like, for example. The dehumidifier section 13 is provided on the wall surface at the back side of the accommodating chamber 11, for example.

The Peltier device 131 is provided in such a way as to partition the inside and the outside of the accommodating chamber 11, and for example, the heat sink fin 132 is attached on the Peltier device 131, on the surface on the outside (the back side) of the chamber, and the attachment section 133 is attached on the Peltier device 131, on the surface on the inside (the front side) of the chamber. The attachment section 133 is formed of a highly thermal conductive metal, for example, and as with the heat sink fin 132, it may be formed into a fin shape where a plurality of metal plates are arranged in parallel. In this case, the plurality of metal plates forming the attachment section 133 are provided each preferably extending in the vertical direction.

At the time of dehumidification of the inside of the accommodating chamber 11, the attachment section 133 is cooled by the Peltier device 131. The surface of the attachment section 133 forms a cooling surface 130 for cooling the air inside the accommodating chamber 11. Specifically, by cooling the temperature of the cooling surface 130 to be around the dew point (for example, around 0° C.), moisture in the air inside the accommodating chamber 11 may be made to condense on the cooling surface 130 (the attachment section 133), and the absolute humidity inside the accommodating chamber 11 may be reduced. At this time, the heat absorbed by the Peltier device 131 from the attachment section 133 is radiated outside the accommodating chamber 11 through the heat sink fin 132.

The tray 134 is for collecting water produced at the time of dehumidification, and is enabled to receive water running down on the attachment section 133 by being arranged below the attachment section 133. Water collected in the tray 134 is drained outside the accommodating chamber 11 via the drainpipe 135.

A cooling fan 14 is provided on the outside of the accommodating chamber 11. In this example, by being attached on the outer wall at the back side of the accommodating chamber 11, the cooling fan 14 is provided near the dehumidifier section 13. The heat sink fin 132 of the dehumidifier section 13 is exposed to the outside from the wall surface at the back side of the accommodating chamber 11, and the cooling fan 14 is provided below the heat sink fin 132.

In the present embodiment, an air passage 15 for letting air pass in the front-back direction is formed below the accommodating chamber 11. The heat sink fin 122 of the cooling section 12 is exposed to the air passage 15 from the wall surface on the lower side of the accommodating chamber 11, and the cooling fan 14 is provided behind the heat sink fin 122 (behind the air passage 15).

The cooling fan 14 includes an air inlet port 141, an air outlet port 142, a blade 143, and the like. During operation of the sample cooling device 1, the air is drawn in from the air inlet port 141 and the air is blown out from the air outlet port 142 by rotation of the blade 143. In this example, the cooling fan 14 is arranged in such a way that the air inlet port 141 is inclined at a predetermined angle (for example, about 45°) with respect to the vertical direction.

Thus, as shown by arrows in FIG. 1, a flow F1 of air flowing downward from the side of the heat sink fin 132 of the dehumidifier section 13 arranged above the cooling fan 14, and a flow F2 of air flowing toward the back from the side of the heat sink fin 122 of the cooling section 12 arranged before the cooling fan 14 are generated. With the generation of such flows F1 and F2 of air, the heat sink fins 122 and 132 as heat generating sections may be cooled.

The heat sink fin 132 of the dehumidifier section 13 is covered with a casing 136. A vent hole 137 for passing air to the heat sink fin 132, and a guide passage 138 for guiding the air which has passed through the heat sink fin 132 to the cooling fan 14 are formed to the casing 136. Thus, the flow F1 of air from the side of the heat sink fin 132 of the dehumidifier section 13 to the cooling fan 14 may be desirably generated. Additionally, this casing 136 may be shaped in other ways or may be omitted.

In the present embodiment, a communicating pipe 16 for communicating the outside and the inside of the accommodating chamber 11 is provided to the sample cooling device 1. One end of the communicating pipe 16 is connected to the air outlet port 142 of the cooling fan 14. On the other hand, the other end of the communicating pipe 16 is connected to the inside of the accommodating chamber 11. The cooling fan 14 and the communicating pipe 16 thereby form a blower section 100 for sending a part of the air sent from the cooling fan 14 into the accommodating chamber 11.

As shown in FIG. 1, the other end of the communicating pipe 16 is arranged inside the accommodating chamber 11, near the dehumidifier section 13. Accordingly, the blower section 100 may send the air from outside the accommodating chamber 11 to near the cooling surface 130 of the dehumidifier section 13. In this example, the air that is sent from the cooling fan 14 side through the communicating pipe 16 is blown toward the inner wall side of the accommodating chamber 11 from the other end of the communicating pipe 16 and is dispersed, and the dispersed air is cooled by the cooling surface 130 of the dehumidifier section 13.

A hood member 101 is provided inside the accommodating chamber 11, for desirably guiding the air that is blown out from the other end of the communicating pipe 16 to the side of the attachment section 133 (the cooling surface 130) of the dehumidifier section 13. This hood member 101 is provided in such a way as to cover a part (for example, the upper side) of the attachment section 133 of the dehumidifier section 13, and air may thereby be guided desirably to between the plurality of metal plates forming the attachment section 133, and cooling may be efficiently performed. Additionally, this hood member 101 may be shaped in other ways or may be omitted.

As described, according to the present embodiment, by sending air into the accommodating chamber 11 by the blower section 100 from outside the accommodating chamber 11, and cooling the air by the dehumidifier section 13, dehumidified air may be supplied to the inside of the accommodating chamber 11. At this time, with the air sent into the accommodating chamber 11 by the blower section 100 from outside the accommodating chamber 11, the inside of the accommodating chamber 11 may be placed in a pressurized state. The air inside the accommodating chamber 11 may thereby be caused to flow out of the accommodating chamber 11 through, for example, the gap between the parts forming the accommodating chamber 11, and air containing moisture may be prevented from flowing into the accommodating chamber 11 through the gap or the like.

Also, since air that is sent into the accommodating chamber 11 by the blower section 100 from outside the accommodating chamber 11 is cooled by the dehumidifier section 13, dehumidified air is supplied into the accommodating chamber 11, and thus humidity inside the accommodating chamber 11 may be prevented from rising due to the air that is sent in by the blower section 100. Accordingly, air containing moisture may be prevented from flowing into the accommodating chamber 11 from outside the accommodating chamber 11, and the air inside the accommodating chamber 11 may be desirably dehumidified.

Especially, with the present embodiment, air may be sent into the accommodating chamber 11 from outside the accommodating chamber 11 by using air that is sent by the cooling fan 14 for cooling a heat generating section (for example, the heat sink fins 122, 132 and the like). Therefore, since there is no need to separately provide a fan or the like to send air into the accommodating chamber 11 from outside the accommodating chamber 11, the manufacturing cost may be reduced.

As in the present embodiment, in the case where the cooling fan 14 is for cooling a heat generating section (the heat sink fin 132) at the dehumidifier section 13, the cooling fan 14 and the dehumidifier section 13 are placed relatively close to each other. Accordingly, a part of the air sent by the cooling fan 14 may be cooled at the dehumidifier section 13 by a simple configuration, and dehumidified air may be supplied into the accommodating chamber 11. The configuration may thus be simplified, and the manufacturing cost may be further reduced.

Also, according to the present embodiment, air sent into the accommodating chamber 11 by the blower section 100 from outside the accommodating chamber 11 is sent to near the cooling surface 130 of the dehumidifier section 13 for cooling the air inside the accommodating chamber 11, and is thus desirably cooled at the cooling surface 130. Therefore, sufficiently dehumidified air may be supplied into the accommodating chamber 11, and thus humidity inside the accommodating chamber 11 may be effectively prevented from rising due to the air that is sent in by the blower section 100.

The suction mechanism 2 is provided with a needle 21 that is to be inserted into the sample container 3. The needle 21 is configured to be able to move in the horizontal and vertical directions, and is inserted into the sample container 3 by being horizontally moved to above the sample container 3 and then moved downward, and the sample inside the sample container 3 is sucked from the needle 21. Then, the needle 21 is moved upward to be removed outside the sample container 3, and is horizontally moved to a sample injection port 22. Then, the sample sucked out from the sample container 3 is injected into the sample injection port 22, and automatic supply of a predetermined amount of sample for analysis is thereby enabled.

According to an autosampler provided with the sample cooling device 1 of the present embodiment, a liquid drain port (not shown) for draining cleaning liquid at the time of cleaning a flow path that is communicated with the needle 21 is formed to a wall surface of the accommodating chamber 11. In this case, when liquid is not being drained from the liquid drain port, air containing moisture may flow into the accommodating chamber 11 from outside the accommodating chamber 11 through the liquid drain port.

However, as in the present embodiment, with a configuration where the inside of the accommodating chamber 11 is to be placed in a pressurized state by air being sent into the accommodating chamber 11 by the blower section 100 from outside the accommodating chamber 11, it is possible to prevent air containing moisture from flowing into the accommodating chamber 11 from outside the accommodating chamber 11 through the liquid drain port.

The embodiment above describes a direct-cooling sample cooling device 1 where the cooling section 12 configures the installation section 123 for installing the sample container 3. However, such a configuration is not restrictive, and the present invention may also be applied to an air-cooling sample cooling device which cools the sample container 3 by air.

The sample container 3 is not limited to be cooled while being held by the rack 4, and it may also be cooled while being directly installed in the installation section 123, for example. Also, the Peltier device 121 for cooling the sample container 3 at the cooling section 12, and the Peltier device 131 for cooling the air at the dehumidifier section 13 are both replaceable by a different cooler.

The blower section 100 is not limited to be configured from the cooling fan 14 and the communicating pipe 16, and may adopt various other configurations. For example, a configuration where a device capable of sending air into the accommodating chamber 11 from outside the accommodating chamber 11 at a predetermined air pressure is separately provided is also possible. In this case, a configuration where air that is dehumidified in advance is sent into the accommodating chamber 11 is also possible.

Also, in the embodiment described above, the cooling fan 14 for cooling the heat generating section (the heat sink fin 132) of the dehumidifier section 13 and the heat generating section (the heat sink fin 122) of the cooling section 12 configures the blower section 100, but the blower section 100 may alternatively be configured from a cooling fan for cooling one of the heat generating sections of the dehumidifier section 13 and the cooling section 12. Also, the blower section 100 may be configured from a cooling fan for cooling a heat generating section other than the heat generating sections of the dehumidifier section 13 and the cooling section 12.

In the case of sending air into the accommodating chamber 11 from outside the accommodating chamber 11 by using various fans, a configuration where a part of the air that is sent to the air inlet port side is sent to the accommodating chamber 11 is also possible, in addition to a configuration as described above where a part of the air that is blown out from the air outlet port side is sent into the accommodating chamber 11.

Furthermore, it is possible to send dehumidified air into the accommodating chamber 11 by providing a desiccant such as silica gel in a flow path for sending air into the accommodating chamber 11 (for example, in the communicating pipe 16). As a configuration for sending dehumidified air into the accommodating chamber 11 as described above, a configuration where a mechanism for cooling the air that is to be sent into the accommodating chamber 11, such as a desiccating mechanism, is provided in a flow path for sending air into the accommodating chamber 11, instead of the desiccant, is also possible.

Any configuration is allowed as long as air that is to be sent into the accommodating chamber 11 by the blower section 100 from outside the accommodating chamber 11 is cooled and dehumidified by the dehumidifier section 13 before being supplied into the accommodating chamber 11, and the configuration of the embodiment described above where air is blown toward the inner wall side of the accommodating chamber 11 from the other end of the communicating pipe 16 is not restrictive.

DESCRIPTION OF REFERENCE SIGNS

1 sample cooling device
2 suction mechanism
3 sample container
4 rack
11 accommodating chamber
12 cooling section
13 dehumidifier section
14 cooling fan
15 air passage
16 communicating pipe
21 needle
22 sample injection port
100 blower section
101 hood member
111 opening/closing cover
121 Peltier device
122 heat sink fin
123 installation section
130 cooling surface
131 Peltier device
132 heat sink fin
133 attachment section
134 tray
135 drainpipe
136 casing
137 vent hole
138 guide passage
141 air inlet port
142 air outlet port
143 blade

The invention claimed is:

1. A sample cooling device for cooling a sample in a sample container that is accommodated in an accommodating chamber, the sample cooling device comprising:
   a cooling section configured to cool the sample container that is accommodated in the accommodating chamber;
   a dehumidifier section configured to perform dehumidification by cooling air inside the accommodating chamber; and
   a blower section configured to supply dehumidified air into the accommodating chamber by sending air into the accommodating chamber from outside the accommodating chamber and outside the sample cooling device, causing the air to be cooled by the dehumidifier section.

2. The sample cooling device according to claim 1, wherein the blower section sends a portion of the air that is sent from a cooling fan for cooling a heat generating section into the accommodating chamber.

3. The sample cooling device according to claim 1,
   wherein the dehumidifier section includes a cooling surface for cooling air inside the accommodating chamber, and
   wherein the blower section sends air from outside the accommodating chamber to near the cooling surface.

4. An autosampler comprising:
   the sample cooling device according to claim 1; and
   a suction mechanism configured to suck a sample inside the sample container that is accommodated in the accommodating chamber.

* * * * *